United States Patent
Bloom et al.

(10) Patent No.: US 7,476,218 B2
(45) Date of Patent: Jan. 13, 2009

(54) SYRINGE WITH LOCKING MEMBER

(75) Inventors: Adam Bloom, Willesden Green (GB); Karen Hamling, Willesden Green (GB)

(73) Assignee: Intra-Tech Healthcare Limited, Park Royal, London (GB)

( * ) Notice: Subject to any disclaimer, the term of this patent is extended or adjusted under 35 U.S.C. 154(b) by 455 days.

(21) Appl. No.: 10/558,456

(22) PCT Filed: May 27, 2004

(86) PCT No.: PCT/GB2004/002283

§ 371 (c)(1), (2), (4) Date: Nov. 28, 2005

(87) PCT Pub. No.: WO2004/105841

PCT Pub. Date: Dec. 9, 2004

(65) Prior Publication Data

US 2006/0264837 A1 Nov. 23, 2006

(30) Foreign Application Priority Data

May 29, 2003 (GB) .................. 0312239.7
Aug. 7, 2003 (GB) .................. 0318485.0

(51) Int. Cl.
*A61M 5/00* (2006.01)
(52) U.S. Cl. ...................... 604/208; 604/110
(58) Field of Classification Search .......... 604/208, 604/209, 210, 246, 110
See application file for complete search history.

(56) References Cited

U.S. PATENT DOCUMENTS

| | | | |
|---|---|---|---|
| 2,627,757 A * | 2/1953 | Austin .................. 74/565 |
| 4,246,898 A * | 1/1981 | Travalent et al. ............ 604/210 |
| 4,275,729 A | 6/1981 | Silver et al. |
| 4,444,335 A * | 4/1984 | Wood et al. .................... 222/43 |
| 4,475,905 A * | 10/1984 | Himmelstrup .............. 604/208 |
| 4,563,178 A * | 1/1986 | Santeramo .................. 604/208 |
| 4,654,035 A * | 3/1987 | Ando ......................... 604/210 |
| 4,874,385 A * | 10/1989 | Moran et al. ................. 604/208 |
| 5,106,379 A * | 4/1992 | Leap .......................... 604/198 |
| 5,222,945 A | 6/1993 | Basnight |
| 5,246,011 A * | 9/1993 | Caillouette .................. 600/566 |
| 5,328,486 A * | 7/1994 | Woodruff .................... 604/208 |
| 5,344,409 A * | 9/1994 | Ennis et al. ................. 604/210 |
| 5,385,558 A | 1/1995 | Cottone et al. |
| 5,531,691 A | 7/1996 | Shonfeld |
| 5,531,708 A | 7/1996 | Woodruff |
| 5,599,314 A * | 2/1997 | Neill .......................... 604/207 |
| 5,925,032 A | 7/1999 | Clements |

FOREIGN PATENT DOCUMENTS

CH 276 860 A 7/1951

(Continued)

*Primary Examiner*—Nicholas D Lucchesi
*Assistant Examiner*—Aarti Bhatia
(74) *Attorney, Agent, or Firm*—Drinker Biddle & Reath LLP

(57) ABSTRACT

A syringe for dispensing a fluid comprising: a barrel for containing the fluid; a plunger having a plunger head slideably mounted and retractable within the barrel; and locking means. The locking means includes fixing means which, when engaged, permanently prevent retraction of the plunger head relative to the barrel beyond a predetermined distance, thereby limiting the travel of the plunger head.

24 Claims, 8 Drawing Sheets

FOREIGN PATENT DOCUMENTS

| | | |
|---|---|---|
| EP | 0 064 858 A | 11/1982 |
| EP | 0 493 639 A | 7/1992 |
| EP | 0 543 156 A | 5/1993 |
| WO | WO 01/23017 A | 4/2001 |
| WO | WO 02/087670 | 11/2002 |
| WO | WO 03/057287 A | 7/2003 |

* cited by examiner

SYRINGE WITH LOCKING MEMBER

BACKGROUND OF THE INVENTION

The present invention relates to syringes. In particular, but not exclusively, the invention relates to syringes having means to limit the dose that may be dispensed by the syringe.

Pre-filled syringes of medicine are supplied to hospitals and other medical centres. Syringes are generally available in a number of standard sizes to provide such doses as 1, 3, 5, 10, 20, 30 and 50 ml. An individual patient may require a dose which is not one of these standard volumes. Therefore, a combination of standard doses will be supplied. This adds to the cost of treatment and causes greater discomfort to the patient. Combining standard doses can also cause error in the dosage applied, and lead to a decrease in accuracy of the dosage dispensed.

It is known to provide standard syringes which include a clamping device mounted to the plunger to limit the volume of fluid that is dispensed, thereby allowing non-standard dosages. These clamping devices are selectively positionable along the plunger at discrete locations. However, accidental movement of the clamping device can occur. Also, for disposable syringes, it is advantageous to provide a simple method of permanently locking the clamping device at a specific dosage.

BRIEF SUMMARY OF THE INVENTION

It is advantageous to provide a pre-filled syringe including a locking device which may only be fitted at the time of assembly and filling. Once assembled and filled, it is preferable that the locking device be operated for permanent locking such that the syringe can not be altered by a user of the syringe.

According to a first aspect of the present invention there is provided a syringe for dispensing a fluid comprising:
 a barrel for containing the fluid;
 a plunger having a plunger head slidably mounted and retractable within the barrel; and
 locking means, wherein:
 the locking means includes fixing means which, when engaged, permanently prevent retraction of the plunger head relative to the barrel beyond a predetermined distance, thereby limiting the travel of the plunger head.

Preferably the locking means comprises a locking member provided at the plunger, and the fixing means comprises means to prevent sliding of at least a portion of the locking member relative to the plunger.

In a first embodiment of the present invention, the sliding prevention means comprises one or more teeth provided at the locking member for embedding into the plunger to permanently fix the locking member relative to the plunger. Preferably the fixing means further comprises means to prevent removal of the locking member from the plunger. Preferably the removal prevention means comprises a permanent lock.

Preferably the locking member comprises two hinged portions and the permanent lock is provided opposite the hinge. Preferably the permanent lock comprises a resilient tab positioned at one of the hinged portions and a slot positioned at the other of the hinged portions. Preferably the resilient tab includes a number of barbs that interlock with a number of detent members provided at an internal surface of the slot. Closing of the hinged portions causes the resilient tab to locate in the slot to prevent further opening of the hinged portions. Preferably the permanent lock is tamper-proof.

Preferably the plunger comprises a plurality of webs extending radially from a central axis of the plunger. Preferably the locking member includes a portion that is complementary in profile to the plunger for mounting the locking member to the plunger. Preferably at least a portion of the plunger is cruciform and each hinged portion of the locking member includes an oversized slot for receiving an arm of the cross. Closing of the hinged portions with each slot receiving an arm of the cross results in enclosure of a section of the plunger by the locking member.

Preferably the locking member is provided with dosage indicating means.

Preferably at least the locking member is formed from a polymer.

In a second embodiment of the present invention, the locking means comprises a longitudinal rail member provided at the plunger, and a locking member slidably mounted to the rail member. Preferably the locking member comprises a locking ring provided around the rail member.

Preferably the rail member is formed integrally with the plunger.

Preferably the rail member is provided substantially along all of the length of the plunger. Preferably the rail member is integral with the plunger at each longitudinal end, and is spaced apart from the plunger between each end.

Preferably the rail member is provided between two adjacent webs of the plunger. Preferably the rail member is adapted to fit into the quadrant defined by two arms of the cruciform plunger and the barrel.

Alternatively the rail member comprises a longitudinal insert. Preferably the rail member includes one or more mounting members for mounting the insert to the plunger. Preferably the rail member is connected to one or more mounting members at each longitudinal end, and is spaced apart from the mounting members between each end.

Preferably the rail member includes a plurality of corrugations to form graduations along the rail member. Preferably the corrugations are spaced such that each graduation corresponds to a predetermined change in the volume defined by the barrel and plunger head. The predetermined distance is proportional to the predetermined change in volume. Preferably the predetermined change in volume is 1 milliliter or more.

Preferably the lateral width of the rail member is greater than the depth of the rail member. Preferably the corrugations are provided only at the lateral sides of the rail member. Preferably an engaging member protrudes from one portion of the internal surface of the locking ring. Preferably the locking ring is adapted to freely slide along the rail member when the locking ring is at a first orientation such that the engaging member does not engage with the corrugations. Preferably the locking ring is further adapted to prevent sliding along the rail member when the locking ring is at a second orientation such that the engaging member engages with the corrugations. Preferably the locking ring includes indenting means such that the locking ring permanently prevents sliding along the rail member when the locking ring is at the second orientation.

Preferably the indenting means comprises an internal indent member provided at a guiding surface of the locking ring. Preferably the indenting means comprises an external indent member for engaging with a portion of the rail member. Preferably the external indent member is engageable with a side rail of the rail member.

Preferably the locking ring includes an arm extending from the outer circumference of the ring. Preferably the arm provides means for rotating the locking ring when mounted to the rail member. Preferably the arm further provides a stop which contacts the barrel when the plunger head is advanced into the barrel. Therefore, the arm limits the travel of the plunger head.

According to a second aspect of the present invention there is provided a locking member for a syringe, the syringe having a barrel for containing a fluid, and a plunger having a plunger head slidably mounted and retractable within the barrel, the locking member being provided at the plunger or barrel and provided with fixing means which, when engaged, permanently prevent retraction of the plunger head relative to the barrel beyond a predetermined distance, thereby limiting the travel of the plunger head.

BRIEF DESCRIPTION OF THE DRAWINGS

Embodiments of the present invention will now be described, by way of example only, with reference to the accompanying drawings, in which.

DETAILED DESCRIPTION

Figure 1:
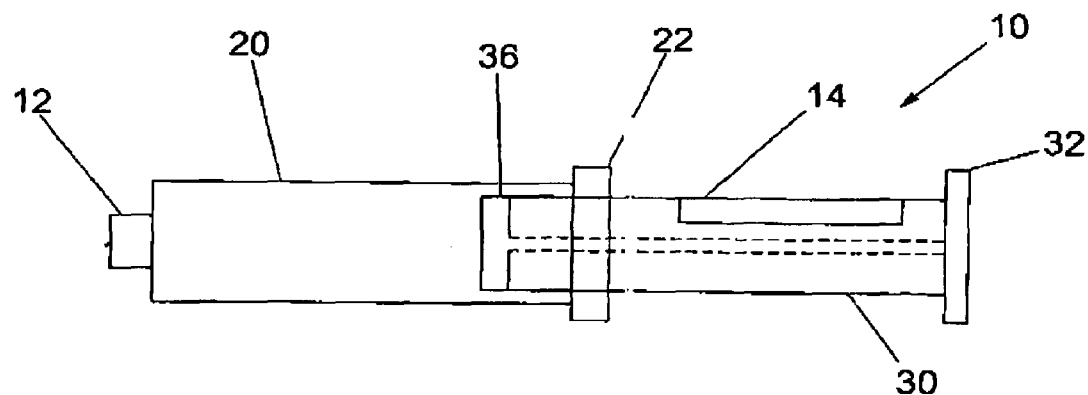
FIG. 1 shows a longitudinal view of a syringe according to the prior art.

Referring to FIG. 1, there is shown a syringe 10 according to the prior art. The syringe 10 includes a barrel 20 that contains the fluid to be dispensed from the nozzle 12 of the syringe 10. Slidably mounted within the barrel 20 is the plunger head 36 of a plunger 30. The plunger 30 includes a grip 32 located at the far end of the plunger 30 for extracting the plunger 30 out of, and retracting the plunger 30 into, the barrel 20. The plunger 30 includes a scale 14 for indicating the volume of fluid that is dispensed. The plunger head 36 sealingly engages with the barrel 20 in a known manner.

FIG. 1 shows the syringe 10 with the plunger 30 fully extended. The plunger 30 is free to slidably retract into the barrel 20 until the grip 32 makes contact with an end stop 22 provided on the barrel 20.

Figure 2:
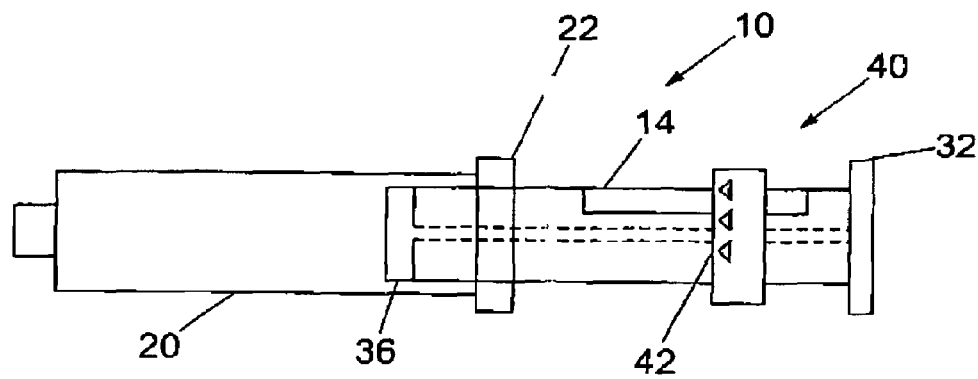
FIG. 2 shows a longitudinal view of a syringe according to a first embodiment of the present invention.
Figure 3:
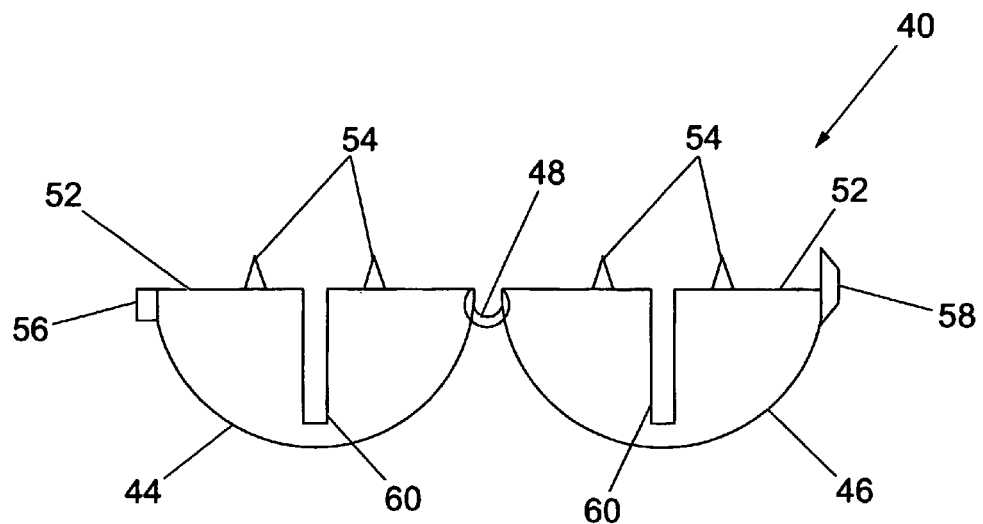
FIG. 3 shows a plan view of the locking member of the syringe of FIG. 2 in a fully opened position.
Figure 4:
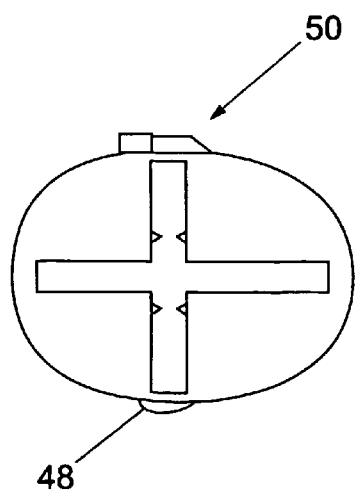
FIG. 4 shows a plan view of the locking member of FIG. 3 in a fully closed position.
Figure 5:
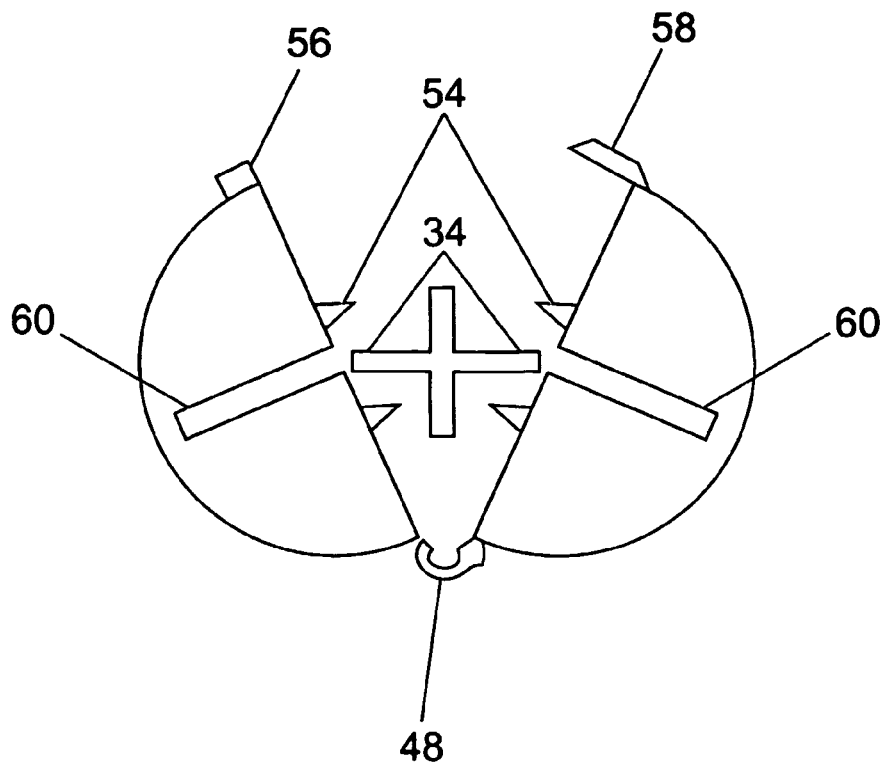
FIG. 5 shows a plan view of the locking member in a partially open position and the plunger of the syringe of FIG. 2.
Figure 6:
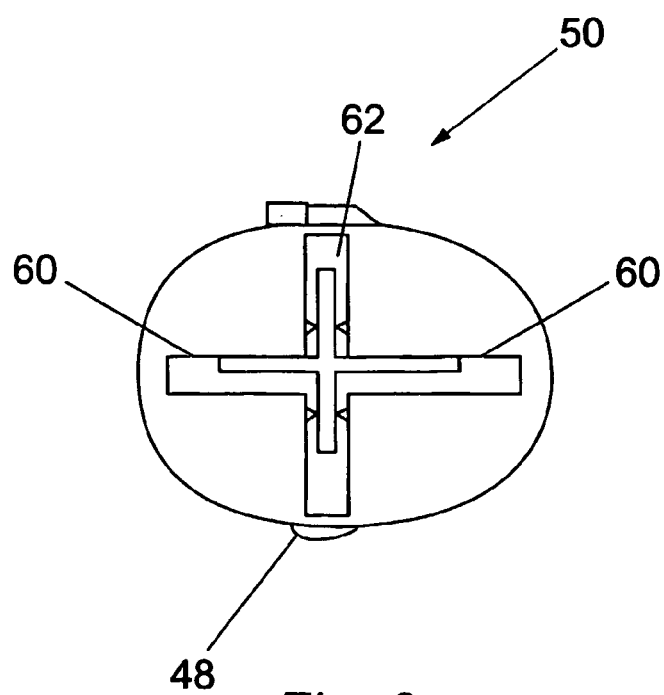
FIG. 6 shows the locking member in a fully closed position and plunger of FIG. 5.

FIG. 2 shows a syringe 10 according to a first aspect of the present invention. The syringe 10 is similar to that of FIG. 1 except for the inclusion of locking means in the form of a locking member 40. Other like features are denoted using like reference numerals.

The locking member 40 is mounted on the plunger and, when it is not engaged as explained below, may be positioned at any location along the plunger 30 between the grip 32 and the end stop 22. As before, a scale 14 is provided on the plunger and dosage indicating means 42 are provided on the locking member 40.

Referring to FIGS. 3 to 6, plan views of the locking member 40 are shown. The locking member 40 comprises two semicircular portions 44, 46 connected together by a hinge 48. Diametrically opposite the hinge, when the two semicircular portions 44, 46 are brought together, is removal prevention means in the form of a permanent lock 50.

Along the abutting edges 52 of the semicircular portions 44, 46 are provided a number of teeth 54. As shown particularly in FIG. 6, these teeth are provided for embedding into the plunger 30 to prevent sliding of the locking member 40 relative to the plunger 30.

Together the teeth 54 and permanent lock 50 provide fixing means to prevent sliding or removal of the locking member 40 relative to the plunger 30. Therefore, retraction of the plunger head relative to the barrel beyond a predetermined distance is permanently prevented.

The permanent lock 50 comprises a resilient tab 58 positioned at one of the hinged portions 44, and a slot 56 located at the other hinged portion 46. The tab 58 includes a number of barbs (not shown) along its length. The slot 56 includes a number of detent members (not shown) provided on an internal surface of the slot 56. As the two hinged portions 44, 46 are brought together, the barbs of the resilient tab 58 interlock with the detent member. In normal use, the two hinged portions 44, 46 are thus permanently locked together. The permanent lock 50 is therefore tamper-proof, as the user is prevented from removing the resilient tab 58 from the slot 56.

Each hinged portion 44, 46 includes a slot 60. A typical plunger 30 is cruciform and the slots 60 are provided to receive an arm 34 of the cross. The slots 60 are oversized relative to the thickness of the arms of the cross so that the arms 34 may be received when the locking member 40 is pivoting towards a closed position.

The hinge 48 and permanent lock 50 are positioned such that, when the locking member is closed, a gap 62 exists between the two hinged portioned 44, 46. Therefore the arms perpendicular to those received in the slots 60 are located in the gap 62. The gap 62 and slots 60 define a portion of the locking member 40 which is complimentary in profile to the plunger 30.

The components of the syringe 10 are typically made from a polymer.

FIGS. 7 to 11 show a second embodiment of the present invention.

The locking member comprises a rail member in the form of a longitudinal insert 70 and a locking ring 90 which may be mounted to the insert 70. However, it is to be appreciated that the rail member may form an integral portion of the plunger 30. The plunger 30 is typically a moulded polymer and the rail member may be included with the plunger 30 during the moulding process.

Figure 7:
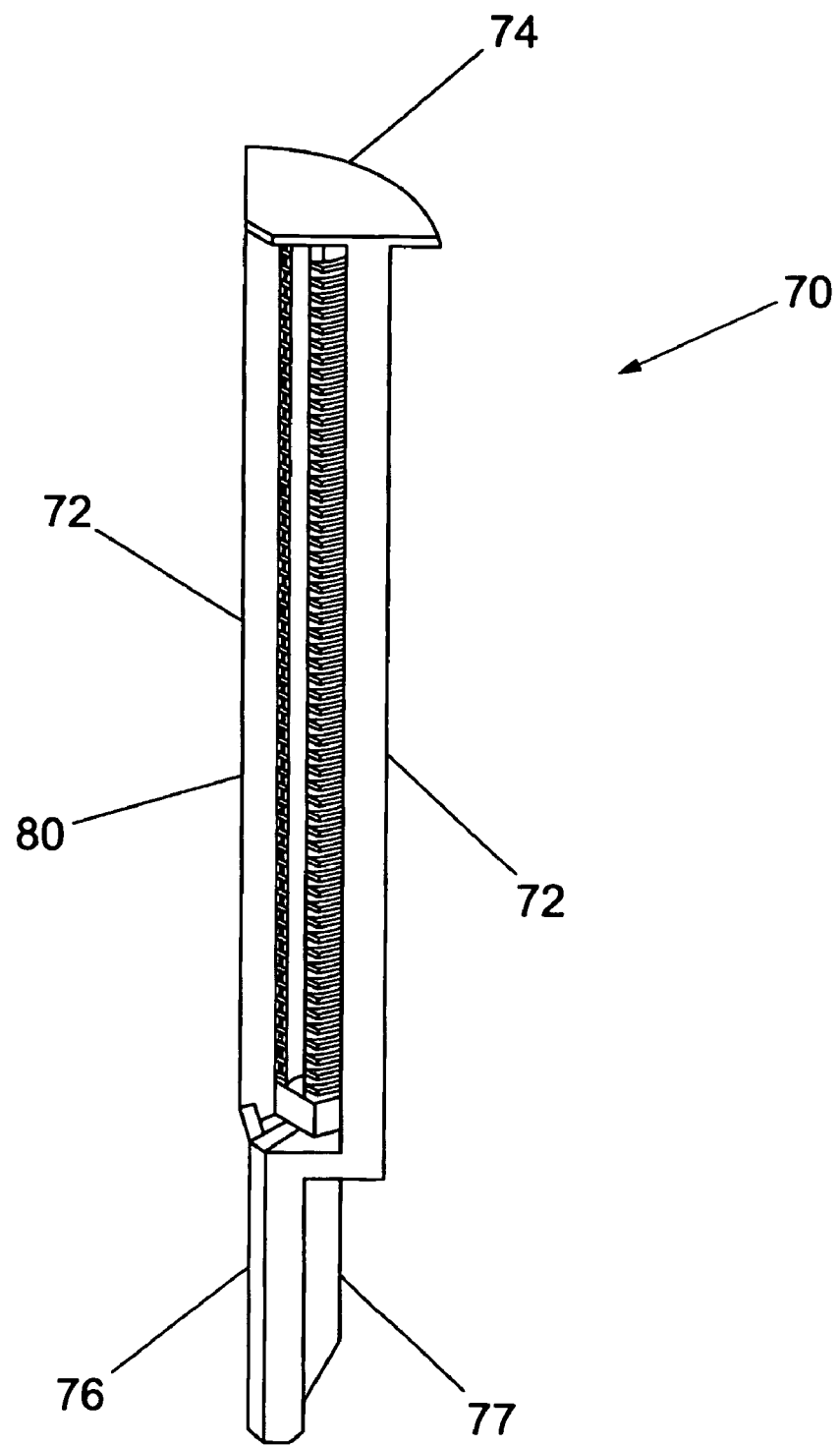
FIG. 7 shows a perspective view of the longitudinal insert of a locking member according to a second embodiment of the present invention.
Figure 9:
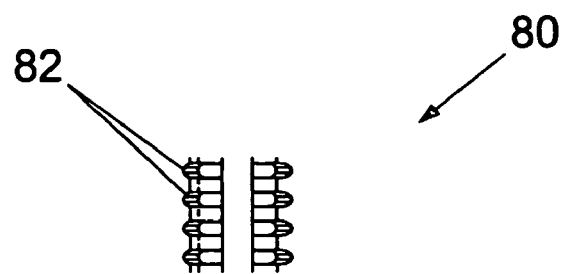
FIG. 9 shows a detailed side view of a portion of the insert of FIG. 7.
Figure 8:
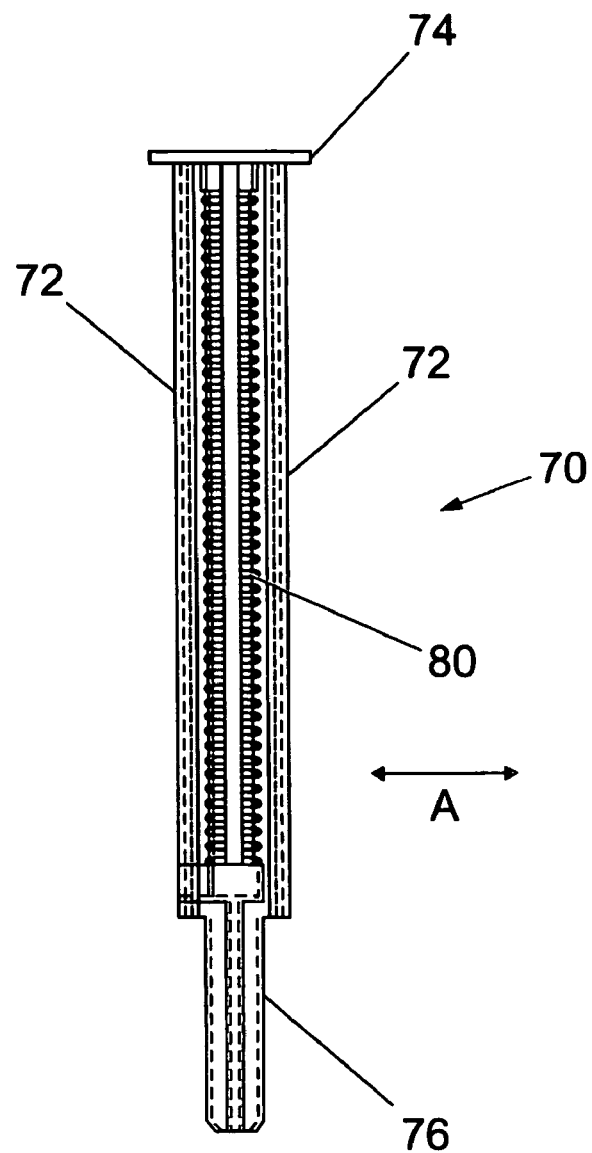
FIG. 8 shows a side view of the insert of FIG. 7.

FIGS. 7 to 9 show the longitudinal insert 70. The insert 70 is adapted to fit into the quadrant defined by two arms 34 of the cruciform plunger 30 and the barrel 20. The insert 70 includes two side rails 72, a top portion 74 and a base portion 76. The side rail 72, top portion 74 and base portion 76 act as mounting members for abutting and mounting the insert 70 to the plunger 30.

The insert 70 further includes a central rail 80 for carrying the locking ring 90. The rail 80 is connected to the top portion 74 and base portion 76 but, as shown in FIG. 8, is spaced apart from the side rails 72.

As best shown in FIG. 9, the rail 80 includes a number of corrugations 82 which form graduations along the rail 80. The spacing of the corrugations are such that each graduation corresponds to a predetermined change in volume defined by the barrel 20 and plunger head 36. The predetermined change in volume is one milliliter. For syringes which provide larger doses, the predetermined change in volume may be greater than one milliliter. Dosage indicating means (not shown) may be provided at the insert 70.

The rail 80 has a greater width (measuring in the direction of arrow A in FIG. 8) than the depth of the rail 80. The corrugations 82 are provided only at the lateral sides of the rail 80.

Figure 10:
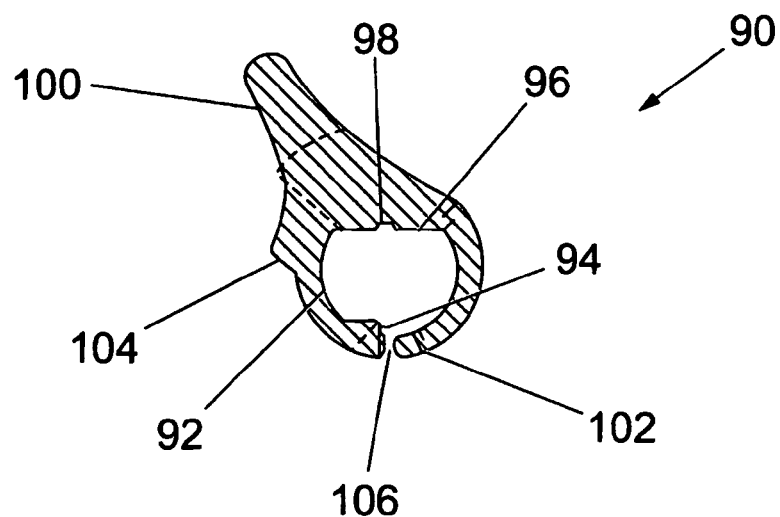
FIG. 10 shows a sectional plan view of the locking ring of a locking member according to a second embodiment of the present invention.
Figure 11:
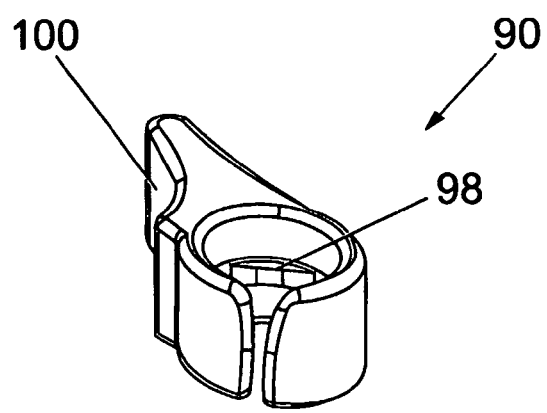
FIG. 11 shows a perspective view of the locking ring of FIG. 10.

FIGS. 10 and 11 show the locking ring 90. Fixing means is provided at the internal surface 92 of the locking ring 90 for fixing the locking ring 90 relative to the insert 70, and therefore the plunger 30. The fixing means comprises an engaging member 94 and a guiding surface 96. At a first orientation of the locking ring, the guiding surface 96 and engaging member 94 are adjacent the surfaces of the rail member, the distance between which define the depth of the rail 80. This depth is less than the distance between the guiding surface 96 and engaging member 94 and therefore the locking ring is free to slide along the rail 80. When the locking ring 90 is rotated towards a second orientation, the guiding surface 96 comes into contact with the lateral sides of the rail 80 due to the greater width of the rail 80. The available internal distance is gradually decreased by the guiding surface 96 as rotation occurs. The locking ring 90 is permanently fixed at the second orientation as the engaging member fully engages with the corrugations 82 at one lateral side and an edge of the opposing lateral side is forced into an internal indent 98 provided at the guiding surface 96.

Figure 12:
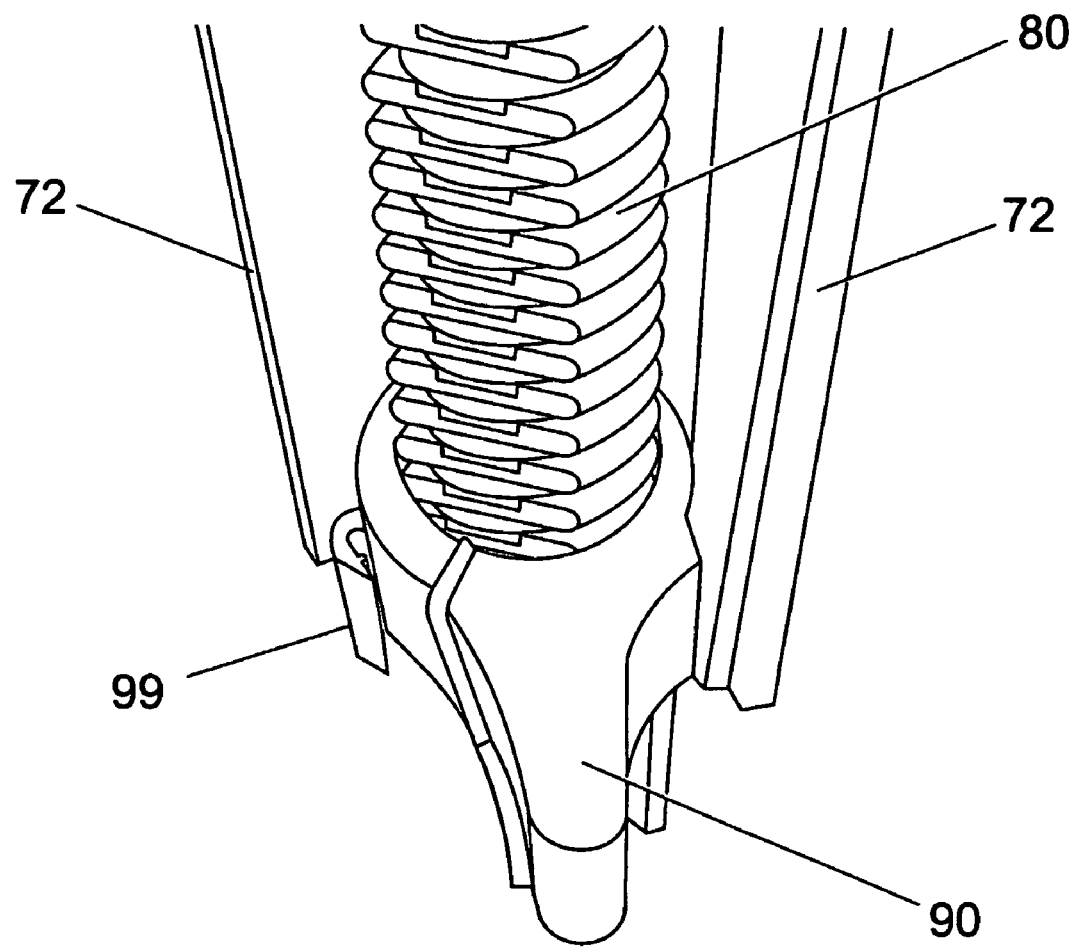
FIG. 12 shows a perspective view of an alternative locking ring at a first orientation.
Figure 13:
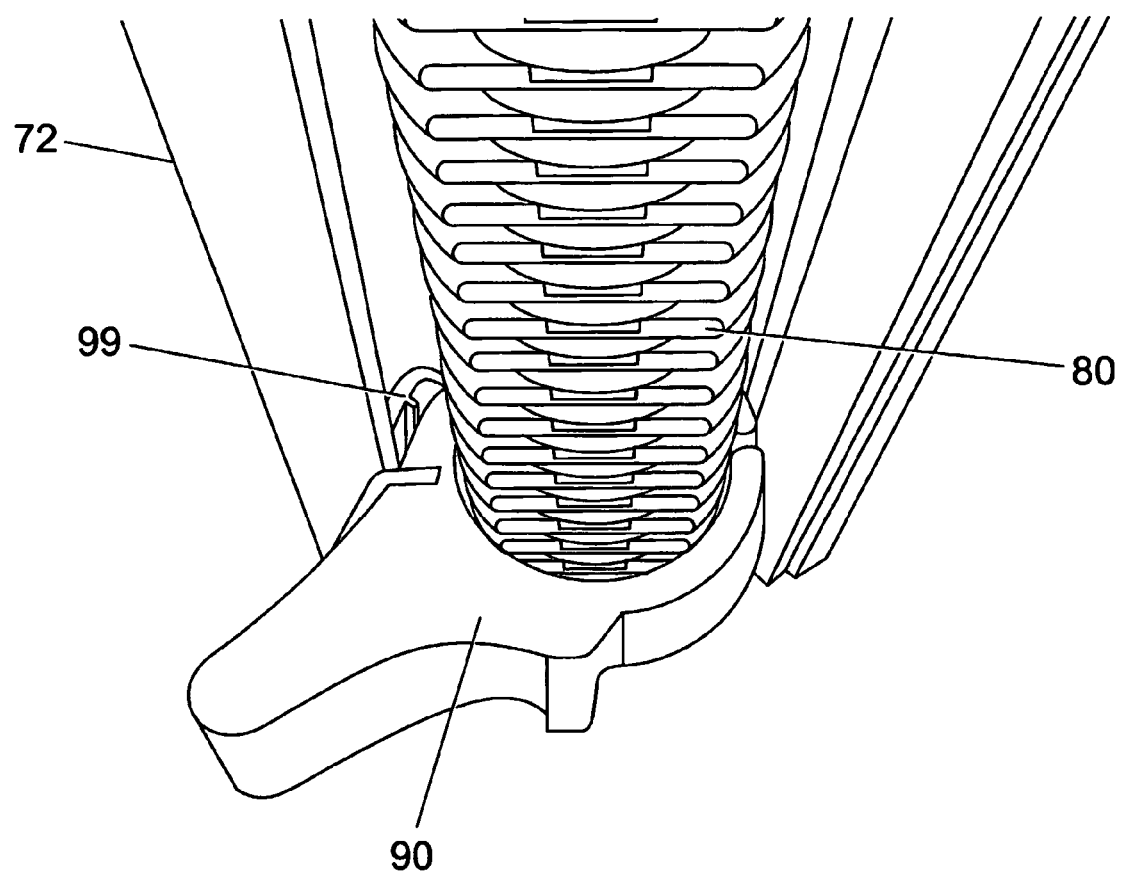
FIG. 13 shows a perspective view of the alternative locking ring of FIG. 12 at a second orientation.

For additional permanent fixing at the second orientation, an external indent provided by a resilient tab 99 may be provided at the locking ring 90 and this is shown in FIGS. 12 and 13. The tab 99 resiliently deforms and then engages with a side rail 72 as the locking ring 90 is moved from the first to the second orientation.

The locking ring 90 includes an arm 100 which extends from the outer circumference 102 of the locking ring 90. This arm 100 provides means for rotating the locking ring 90 when it is mounted to the rail member 80. When the locking ring 90 has been permanently fixed relative to the insert 70, the arm 100 also provides a stop when the plunger head 36 is advanced into the barrel 20. The arm therefore limits the travel of the plunger head 36.

The locking ring 90 further includes a stop surface 104 which contacts a side rail 72 at the second orientation and prevents further rotating of the locking ring 90.

The rail 80 is connected to a web member 77 of the base portion 76. The web member 77 is sufficiently thin such that it can pass through a gap 106 provided at the locking ring 90. This allows fitting of the locking ring 90 to the insert 70. It should be appreciated that the locking ring 90 can only be fitted at the time of assembly and filling of the syringe as the plunger 30 must be fully extracted to expose the web member 77.

The insert 70 can be fitted to the plunger 30 in a number of known ways, such as using an adhesive. The insert 70 and locking ring 90 are typically made from a polymer.

Various modifications and improvements can be made without departing from the scope of the present invention. For example, at least a portion of the locking member may be provided at the barrel.

The invention claimed is:

1. A syringe for dispensing a fluid, comprising:
   a barrel for containing the fluid;
   a plunger having a plunger head slideably mounted and retractable within the barrel;
   selectively engageable locking means,
   wherein the locking means comprises a locking member provided at the plunger, the locking member being rotatable relative to the plunger from a first to a second position,
   wherein the locking member is slidable relative to the plunger when the locking member is at the first position,
   and wherein the locking member is prevented from sliding relative to the plunger when the locking member is at the second position, thereby limiting the travel of the plunger head to determine the volume of fluid that is dispensed;
   and wherein the syringe includes:
   fixing means comprising a resilient tab, that when engaged permanently prevents movement of the locking member from the second position to the first position.

2. A syringe as claimed in claim 1, wherein the sliding prevention means comprises one or more teeth provided at the locking member for embedding into the plunger to permanently fix the locking member relative to the plunger.

3. A syringe as claimed in claim 1, wherein the locking means includes a longitudinal rail member provided at the plunger, and wherein the locking member comprises a locking ring which is slideably mounted to the rail member.

4. A syringe as claimed in claim 3, wherein the rail member is formed integrally with the plunger.

5. A syringe as claimed in claim 4, wherein the rail member is integral with the plunger at each longitudinal end, and is spaced apart from the plunger between each end.

6. A syringe as claimed in claim 3, wherein the plunger is cruciform and the rail member is adapted to fit into the quadrant defined by two arms of the cruciform plunger and the barrel.

7. A syringe as claimed in claim 3, wherein the rail member comprises a longitudinal insert.

8. A syringe as claimed in claim 3, wherein the rail member includes a plurality of corrugations to form graduations along the rail member.

9. A syringe as claimed in claim 8, wherein the corrugations are spaced such that each graduation corresponds to a predetermined change in the volume defined by the barrel and plunger head.

10. A syringe as claimed in claim 8, wherein the lateral width of the rail member is greater than the depth of the rail member, and wherein corrugations are provided at the lateral sides of the rail member.

11. A syringe as claimed in claim 3, wherein an engaging member protrudes from one portion of the internal surface of the locking ring such that the locking ring is adapted to freely slide along the rail member when the locking ring is at a first orientation.

12. A syringe as claimed in claim 11, wherein the locking ring includes indenting means such that the locking ring permanently prevents sliding along the rail member when the locking ring is at a second orientation.

13. A syringe as claimed in claim 12, wherein the indenting means comprises an internal indent member provided at a guiding surface of the locking ring.

14. A syringe as claimed in claim 12, wherein the indenting means comprises an external indent member for engaging with a portion of the rail member.

15. A syringe as claimed in claim 14, wherein the external indent member is engageable with a side rail of the rail member.

16. A syringe as claimed in claim 3, wherein the locking ring includes an arm extending from the outer circumference of the ring, the arm providing means for rotating the locking ring when mounted to the rail member.

17. A syringe as claimed in claim 16, wherein the arm further provides a stop which contacts the barrel when the plunger head is advanced into the barrel.

18. A syringe as claimed in claim 1, wherein the locking member comprises two hinged portions and a permanent lock is provided opposite the hinge to prevent removal of the locking member from the plunger.

19. A syringe as claimed in claim 18, wherein the locking member includes a portion that is complementary in profile to the plunger for mounting the locking member to the plunger.

20. A syringe as claimed in claim 19, wherein each hinged portion of the locking member includes an oversized slot for receiving an arm of the cruciform plunger.

21. A syringe for dispensing a fluid, comprising:
    a barrel for containing the fluid;
    a plunger having a plunger head slidably mounted and retractable within the barrel;
    a selectively engageable lock that comprises a locking member provided at the plunger, the locking member being rotatable relative to the plunger from a first to a second position,
    wherein the looking member is slidable relative to the plunger when the locking member is at the first position,
    wherein the locking member is prevented from sliding relative to the plunger when the locking member is at the second position, thereby limiting the travel of the plunger head to determine the volume of fluid that is dispensed;
    and wherein the syringe includes a fixer comprising a resilient tab, that when engaged permanently prevents movement of the locking member from the second position to the first position.

22. A syringe as claimed in claim 21, wherein the locking means includes a longitudinal rail member formed integrally with the plunger, and wherein the locking member comprises a locking ring which is slidably mounted to the rail member wherein the rail member is integral with the plunger at each longitudinal end, and is spaced apart from the plunger between each end.

23. A syringe as claimed in claim 21, wherein the plunger is cruciform, wherein the lock includes a longitudinal rail member adapted to fit into the quadrant defined by two arms of the cruciform plunger and the barrel, and wherein the locking member is slidably mounted to the rail member.

24. A syringe as claimed in claim 21, wherein the locking means includes a longitudinal rail member provided at the plunger, wherein the locking member includes an arm extending from the outer circumference of the ring; wherein the rotation of the locking member can be effected using the arm when mounted to the rail member, and wherein the arm further provides a stop which contacts the barrel when the plunger head is advanced into the barrel.

* * * * *